United States Patent
Kirsch et al.

(10) Patent No.: US 6,589,762 B1
(45) Date of Patent: Jul. 8, 2003

(54) CALCAFLUOR SCREEN FOR CHITIN BIOSYNTHESIS INHIBITORS

(75) Inventors: Donald Richard Kirsch, Princeton, NJ (US); Margaret Hsien-Fen Kuh Lai, East Brunswick, NJ (US); Sanford J. Silverman, Roosevelt, NJ (US)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 08/757,787

(22) Filed: Nov. 27, 1996

Related U.S. Application Data

(63) Continuation of application No. 08/066,576, filed on May 25, 1993, now abandoned.

(51) Int. Cl.[7] ............................................. C12Q 1/18
(52) U.S. Cl. ......................................................... 435/32
(58) Field of Search ............................................. 435/32

(56) References Cited

PUBLICATIONS

Roncero, et al. J Bacteriology, vol. 170, No. 4, pp 1945–1949 (1988).*
Shaw, et al. J Cell Biology, vol. 114, No. 1, pp 111–123 (1991).*
Cabib, Antimicrobial Agents and Chemotherapy vol. 35, No. 1, pp 170–173 (1991).*
Silverman, et al. PNAS, 85:4735–4739 (1988).*
Bulawa, C.E., and Osmond, B.C., Proc. Natl. Acad. Sci. USA 87: 7424–7428 (1990).
Cabib, E., Antimicrob. Agents Chemother. 35: 170–173 (1991).
Correa, J., et al., J. Biol. Chem. 257: 1392–1397 (1982).
Masui, Y., et al., Biochem. Biophys. Res. Com. 78: 534–538 (1977).
Neville, A.C., The Biology of the Arthropod Cuticle, Springer–Verlag, New York, 1975, pp. 71 to 76.
Orlean, P. J. Biol. Chem. 262: 5732–5739 (1987).
Roncero, C., and Duran, A., J. Bact. 163: 1180–1185 (1985).
Roncero, C., et al., J. Bact. 170: 1945–1949 (1988).
Roncero, C., et al., J. Bact. 170: 1950–1954 (1988).
Shaw, J.A., et al., J. Cell Biol. 114: 111–123 (1991).
Silverman, S.J., et al., Proc. Natl. Acad. Sci., U.S.A., 85: 4735–4739 (1988).

* cited by examiner

*Primary Examiner*—Johann Richter
*Assistant Examiner*—Howard V. Owens
(74) *Attorney, Agent, or Firm*—Finnegan, Henderson, Farabow, Garrett & Dunner, L.L.P.

(57) ABSTRACT

A method for the identification of agents which inhibit chitin synthesis, thus exhibiting potential fungicidal and insecticidal activity, involves the incubation of test samples in neutral *Saccharomyces cerevisiae* cultures containing calcofluor white, a fluorochrome that causes lethal chitin hyperpolymerization in the yeast. Cultures containing samples that inhibit chitin synthesis exhibit enhanced growth because the growing fungus is rescued from the adverse effects of calcofluor white. In the practice of the invention, the test sample is added to a *S. cerevisiae* culture or culture area containing calcofluor white and the culture is incubated with the test sample for such time under such conditions sufficient to observe yeast cell growth inhibition in a corresponding culture or culture area containing calcofluor but no test sample. The extent of growth in the culture or culture area containing test sample is then compared with the extent of growth in the culture or culture area containing no test sample, and the presence of chitin synthesis inhibition is determined by observation of whether culture growth in the presence of test sample exceeds growth in its absence. Preferred embodiments employ test samples on disks or in wells in solidified cultures and a known chitin synthesis inhibitor as a positive control which is compared to the test sample.

24 Claims, No Drawings

CALCAFLUOR SCREEN FOR CHITIN BIOSYNTHESIS INHIBITORS

This is a continuation of application Ser. No. 08//066,576 filed on May 25, 1993, now abandoned.

TECHNICAL FIELD OF THE INVENTION

This invention relates to the identification of potential fungicides and insecticides using a screening method that reverses the calcofluor inhibition of chitin biosynthesis in yeast.

BACKGROUND OF THE INVENTION

The polysaccharide chitin is a structural cell wall component of all fungi except some *Basidiomycetes fungi* and most Oomycetes, and is the most abundant organic skeletal component of invertebrates, making up, for example, from about 25 to 60% of the dry weight of insect cuticles. Chitin consists primarily of linear polymers of the amino sugar N-acetyl-D-glucosamine joined in 1,4-β-glucosidic linkage. Thus, chitin bears a close resemblance to cellulose, the major structural polysaccharide of plants; indeed, the only chemical difference between them is that in chitin the hydroxyl group on the 2-position is an acetoamido group instead of an hydroxyl. However, because of its widespread occurrence in fungi and arthropods, the total world-wide production of chitin vastly exceeds cellulose (Neville, A. C., *The Biology of the Arthropod Cuticle*, Springer-Verlag, New York, 1975, pages 71 to 76).

Many fungi and arthropods having chitinous cell walls or exoskeletons are injurious to plants and animals, causing a legion number of diseases. To name but a few, fungal species containing chitin cause wheat eyespot, rice sheath blight, damping off, apple scab, pepper botrytis, rice blast, sugar beet cercospora, tomato early blight, wheat leaf rust, and wheat powdery mildew. Fungal species also cause myriad cutaneous and systemic mycoses in human beings and other animals, including candidiasis, histoplasmosis, blastomycosis, sporotrichosis, cryptococcosis, and the like. Insects are vectors of viruses causing arboviral encephalitides, yellow fever, and dengue, protozoa causing malarias, trypanosomiases, and leishmaniases, and various harmful helminths. Crustaceans carry some infectious helminths and trematodes.

Most fungicides and insecticides that are used to control or cure these diseases by killing or controlling their causative agents, intermediate hosts, or vectors employ various modes of action including physical poisons that suffocate or dessicate organisms; protoplasmic poisons such as arsenicals that kill by precipitating or deactivating proteins, enzymes or other cellular constituents; respiratory poisons that deactivate respiratory enzymes; and various poisons that affect different tissue systems such as tubules or nerves. Of course, preferred agents do not injure the host plant or animal, and most preferably have no effect whatsoever on the host. Because of the complexity and interdependence of life processes, however, this goal is not always achieved, so that many fungicides and insecticides exhibit some toxicity to the host. Others cause unexpected side effects.

Since chitin is not a usual constituent of most plants and vertebrates, chitin biosynthesis inhibitors can be employed as selective antifungal and/or insecticide agents. Applied to ornamental or edible plants or animals, these offer the advantage of targeting undesirable fungi or insects without harming significantly the host plant or vertebrate animal. 1-(2,6-Dichlorobenzoyl)-3-(3,4-dichlorophenyl)urea, for example, has been suggested as a chitin-inhibiting insecticide (Neville, cited above). Antifungals that inhibit chitin synthesis include nikkomycin and polyoxin D.

Calcofluor white is a fluorescent brightener used commercially to whiten textiles and paper. The fluorochrome has been used as a stain for cell wall materials in fungi, algae, and higher plants. It can exhibit antifungal properties, binding to nascent chitin microfibrils in fungal cell walls containing chitin. Exposure of yeast (*Saccharomyces cerevisiae*) to calcofluor white, for example, induces abnormally thick walls between mother and daughter cells during cell division as a result of the massive deposition of anomalous crystallized chitin. The dye interaction appears to enhance the rate of chitin polymerization, producing levels of chitin that are inhibitory to cell growth and viability (Roncero, C., et al., *J. Bact.* 170: 1945–1949 (1988)). Microscopic examination of calcofluor-inhibited cells reveals high levels of chitin deposition. This putative mechanism for calcofluor white action is supported by the observation that mutants selected for calcofluor white resistance show decreased levels of chitin synthesis (Roncero, C., et al., *J. Bact.* 170: 1950–1954 (1988)).

The interaction of calcofluor white with growing *S. cerevisiae* cells generally requires a pH of above 4 and close to 6 or 6.5 (Roncero, et al., cited above at 1946). This can perhaps be understood in view of the fact that a major chitinase in yeast is active only under acidic conditions (Correa, J., et al., *J. Biol. Chem.* 257: 1392–1397 (1982)). It is possible that this enzyme opposes the action of calcofluor, and thus the activity of calcofluor is augmented under conditions of reduced chitinase activity.

SUMMARY OF THE INVENTION

It is an object of the invention to provide a screening test for the identification of agents exhibiting potential fungicidal and insecticidal activity for a wide variety of agricultural, medical, and veterinary uses.

It is a further and more specific object of the invention to identify agents that inhibit chitin biosynthesis.

These and other objects are accomplished by the present invention, which provides a method for the identification of agents which inhibit chitin synthesis, and thus possess fungicidal and insecticidal activity making them potentially suitable as selective fungicides or insecticides. The method is a screening test whereby test samples are incubated in a fungal culture with calcofluor white. Agents exhibiting potentially desirable fungicidal or insecticidal properties inhibit chitin synthesis, and, by doing so, reverse calcofluor white inhibition of the culture. Agents that are positive in the test produce enhanced fungus growth because they rescue the growing fungus from the adverse effects of calcofluor white.

In the practice of this inventive method for screening for the presence or absence of chitin synthesis inhibition by a test sample, the test sample is added to a chitin-producing fungus, e.g., a yeast, culture or culture area containing calcofluor white. The culture is incubated with the test sample for such time under such conditions sufficient to observe yeast cell growth inhibition in a corresponding culture containing calcofluor but no test sample. The extent of growth in the culture or culture area containing test sample is then compared with the extent of growth in the culture or culture area containing no test sample. The presence of chitin synthesis inhibition is determined by observation of whether culture growth in the presence of test sample exceeds growth in its absence.

In a preferred screening test, a *Saccharomyces cerevisiae* strain exhibiting little or no calcofluor white resistance is grown in culture at neutral pH in the presence of calcofluor white and test samples. Potentially active agents are identified by the observation of enhanced growth of the cultured yeast. In especially preferred embodiments, a positive control is employed to assist in the identification of potential agents. In these embodiments, a known chitin sythesis inhibitor such as nikkomycin Z is added to the culture or culture area, and this is compared to the culture with the test sample.

In a particularly preferred embodiment, the yeast is grown in a solidified media in the presence of calcofluor in a plate or dish, so that test samples and positive controls can be observed visually and simultaneously as regions of the same culture. Actives produce a turbid zone of growth around the test sample in the lawn of the culture.

DETAILED DESCRIPTION OF THE INVENTION

This invention is based upon the finding that chemical and biochemical agents of potential value as fungicides or insecticides are identified in *Saccharomyces cerevisiae* cultures containing calcofluor white, a fluorochrome that causes lethal chitin polymerization in the yeast. Cultures containing test samples that inhibit chitin formation exhibit enhanced growth because the test sample rescues the cultured yeast cells from the deleterious effects of calcofluor white.

In the practice of this invention, test samples are incubated in the presence of calcofluor white in cultures of any fungal species that produce chitin, such as unicellular fungi. A preferred method employs common baker's yeast, *Saccharomyces cerevisiae*, because it is readily available and easy to culture. A known chitin synthesis inhibitor is employed as a positive control. Potentially active agents are identified by the observation of enhanced yeast growth.

A preferred method comprises adding a test sample to a *Saccharomyces cerevisiae* culture containing calcofluor white or a calcofluor white derivative. The test sample is introduced to a disk or a well on a culture plate in a standard diffusion assay using solidified media, or introduced into one of a series of equivalent tissue culture tubes or bottles in a standard turbidity assay using liquid media. The culture is incubated for such time under such conditions sufficient to observe yeast cell growth inhibition in a corresponding culture or culture plate area containing calcofluor white but no test sample. The extent of growth of the culture containing or surrounding the test sample is compared with the extent of growth in the culture or culture area containing no test sample. The presence of chitin synthesis inhibition is determined by observing whether growth in the presence of test sample exceeds growth in its absence. In a culture plate, this is a turbid zone of growth surrounding the test sample. In a culture tube series, this is enhanced turbidity.

Preferred methods employ a known chitin synthesis inhibitor such as nikkomycin Z as a positive control. The control is useful in discerning whether the screen is functioning properly and in identifying positives by direct comparison. In a disk or well diffusion assay, the control is introduced to a disk or a well in the culture plate at the same time the test sample is introduced. After the incubation period, growth in the vicinity of the control exceeds growth in the culture where there is no test sample. A test sample that inhibits chitin biosynthesis will exceed growth in the rest of the culture even if it does not approximate or exceed growth in the vicinity of the positive control. Likewise, in a turbidity assay, the control is introduced into an equivalent tissue culture tube or bottle and incubated with test and negative cultures; after incubation, cultures containing a test sample that inhibits chitin biosynthesis exhibit more turbidity than that observed in tubes containing yeast and calcofluor white only, exhibiting enhanced turbidity analogous to that observed with the positive control.

By "calcofluor white" is meant the fluorescent brightener (2,2'-(1,2-ethenediyl)bis[5-[[4-bis (2-hydroxyethyl) amino)-6-(phenylamino)-1,3,5-triazin-2-yl]amino]-benzenesulfonic acid or 4,4'-bis[4-anilino-bis(β-hydroxyethyl) amino-s-triazine-2-ylamino]-2,2'-stilbene disulfonic acid) and its derivatives such as its esters and salts and includes its benzidine derivative, Congo red (3,3'-[[1,1'biphenyl]-4,4'-diylbis(azo)]bis(4-amino-1-naphthalenesulfonicacid]), which has also been shown to activate chitin polymerization in fungal cell walls (Roncero, C., and Duran, A., *J. Bact.* 163: 1180–1185 (1985)). Preferred embodiments employ the disodium salt of calcofluor white, which is commercially available, marketed under the names Calcofluor White M2R, Tinopal LPW, and C.I. 40622.

Calcofluor white is added to *Saccharomyces cerevisiae* cultures in preferred embodiments. Many readily available strains of *S. cerevisiae* may be employed. Strains showing little or no calcofluor white resistance are preferred, especially those sensitive to calcofluor white. Wild-type strains are especially preferred in some embodiments. Typical *S. cerevisiae* strains include, but are not limited to, wild-type strain A.T.C.C. 12341, X2180 (A.T.C.C. 26109), or X2180-1A obtained from the Yeast Genetic Stock Center.

Any type of solidified or liquid media that will support growth and reproduction of *S. cerevisiae* may be employed as cultures in the method of this invention. Numerous yeast media are known to the skilled artisan, and include, for example, yeast basal growth media (YBGM) containing glucose, vitamins, minerals, and water. Preferred media are solidified by adding agar or gelatin; especially preferred are media solidified with agar. Preferred media are buffered and neutral, i.e., have a pH of about 4 to about 8, preferably about 5.5 to about 7.5. In some embodiments, the preferred pH of the media ranges from about 6 to about 7.

Enhanced growth in solidified cultures is ordinarily observed visually as turbid areas of growth around disks or wells in the culture plate. Enhanced growth in liquid cultures is observed visually, but is ordinarily determined spectrophotometrically as enhanced optical density (OD) at about 550 to 650 nm.

A distinct advantage of the invention is its speed and simplicity. Baker's yeast is readily available and inexpensive. Using solidified media in culture plates, the protocol is extremely simple. Many samples can be readily analyzed in a short time.

It is another advantage of the invention that only small amounts of biochemical or chemical agents are required in the test. In a standard assay, for example, which employs solidified media in a plate, as little as 20 $\mu$g of a biochemical or chemical test sample can be applied to a disk or in a well. As a positive control, as little as 2 to 10 $\mu$g of nikkomycin Z can be used. For fermentation broths, little or no concentration is necessary, but may be required for some samples.

It is a further advantage of the invention that the calcofluor rescue assay is a low positive rate assay (<0.02%), so that secondary tests are not of crucial importance. For an identification of a specific mechanism of action for a newly discovered positive test sample, however, it is advantageous to have more than one biological assay method. Moreover, undesired false positives in the calcofluor rescue screen such as those caused by artifacts of compound-calcofluor complexing are avoided by retesting positives obtained in the primary calcofluor rescue screen using secondary assays which detect in vivo or in vitro inhibition of chitin synthases. Preferred secondary assays differ in action from the primary screen and do not use calcofluor, so they are used to identify chitin synthesis inhibitors that do not act directly on calcofluor. Especially preferred secondary tests assay for chitin synthase inhibition by test samples that inhibit chitin in the primary calcofluor rescue screen. Most especially preferred secondary tests identify the chitin synthase isozyme affected by positive test samples.

One type of calcofluor rescue secondary screen is an in vivo test that assays the effect of compounds on the growth of chitin synthase mutant yeast strains that rely on a single chitin synthase isozyme for survival. A number of these strains have been described, such as the strains that rely on chitin synthase isozymes 2 or 3 described by Shaw, J. A., et al. (J. Cell Biol. 114: 111–123 (1991)) and similar strains described in the Examples section below. In this type of secondary screening test, the test sample added to and incubated in a culture of a mutant yeast strain producing only chitin synthase 2 or 3 (denoted, respectively, Chs2 and Chs3) for such time under such conditions sufficient to observe growth in a corresponding culture containing no test sample. A comparison of the extent of growth in the culture containing test sample with growth in its absence is then made. Inhibition of growth in the presence of test sample indicates inhibition of synthase isozyme produced by the strain. Any type of growth assessment may be employed but, as in the primary calcofluor rescue screen, preferred cultures in the secondary screen are solid, with test samples applied to a disk or well, so that cell growth can be easily determined by visual inspection.

Especially preferred in vivo secondary screens employ a pair of genetically related strains, one producing one isozyme, e.g., Chs2, and the other producing a different isozyme, e.g., Chs3. Using pairs allows for the simultaneous determination that culture conditions are appropriate for growth in the absence of inhibition and the identification of which isozyme may be affected by inhibition. The pairs, for example, include the ECY36-3C and ECY36-3D strains described by Shaw, cited above, that produce only Chs3 and Chs 2, respectively, and similar pairs such as SSY640-10A (containing only Chs3) and SSY-638-3B (containing only Chs 2) described in the Examples below. When nikkomycin Z, an inhibitor of chitin synthase active in the primary screen and known to inhibit the activity of Chs1 to a much greater extent than Chs2 (Cabib, E., *Antimicrob. Agents Chemother.* 35: 170–173 (1991)) is incubated in these culture pairs, it is found that strains ECY36-3C or SSY640-10A are inhibited, whereas growth of either strain ECY36-3D or SSY638-3B is unaffected by the compound. Thus, nikkomycin Z inhibits Chs3 to a significantly greater extent than Chs2. In a similar manner, a comparison of differential effects observed in the growth of strain pairs in the presence of a test sample allows for the putative identification of which isozyme is affected by the sample.

Alternatively and/or additionally, test samples that are positive in the primary calcofluor rescue screen can be tested in an in vitro enzyme assay for chitin synthase. Any type of chitin synthase assay can be employed, such as uptake of radioactively labelled N-acetylglucosamine chitin subunits, or N-acetylglucosamine precursors or derivatives such as uridine diphospho-N-acetylglucosamine, into chitin (described by Orlean, P., *J. Biol. Chem.* 262: 5732–5739 (1987)). The assays of this type are generally conducted in the particulate fraction of yeast cells or in isolates of the particulate fraction. Chitin synthase activity is determined after incubation in a buffered assay mixture. The chitin product is quantified by filtration followed by scintillation counting. Detailed descriptions are given hereinafter.

To assist in the identification of the mechanism of action of a test sample that is positive in the primary calcofluor rescue screen, enzyme assays for individual isozymes Chs1, Chs2, and Chs3 are preferred. Isozyme assays employ, as the yeast cells supplying enzyme, mutant strains expressing only one isozyme, such as those listed above for the in vivo assay. Thus, to measure Chs2 activity, chs1, chs3 mutants such as ECY36-3D or SSY638-3B producing Chs2, or a cell that carries a high-copy plasmid with the CHS2 gene such as SSY563-9B described below are used to supply enzyme. Similarly, Chs3 activity is measured using membranes from cells lacking Chs1, and preferably Chs2, such as strains ECY36-3C containing Chs3 or SSY640-10A described below. To assay Chs1 activity, it is sufficient to use a wild-type strain, as this isozyme is the major in vitro chitin synthase. Detailed descriptions are given hereinafter.

Standard in vitro and in vivo fungicide discovery screens are employed as tertiary tests to prioritize actives from the calcofluor rescue screen and the secondary screens. These in vitro screens test samples for their ability to inhibit the growth of selected phytopathogenic fungi cultured in nutrient agar. These include fungi causing wheat eyespot (*Pseudocercosporella herpotrichoides*), rice sheath blight (*Rhizoctonia solani*) and damping off (*Fusarium oxysporum*); all synthesize chitin-containing cell walls. High potency fungicides are active against these species in the 10 ppm range (10 $\mu$g/ml), while nikkomycin Z can be detected at ~70 $\mu$g/ml in the calcofluor rescue assay if 30 $\mu$l volumes are tested in welled plates. Polyoxin D shows excellent activity in the 10 $\mu$g/ml concentration range (especially against Rhizoctonia), although nikkomycin Z is only weakly active at 25 $\mu$g/ml.

In in vivo screens, a variety of phytopathogenic fungi are used to infect plants treated with test compounds. Active compounds block or reduce the appearance of disease symptoms. A number of model plant infections are employed in the screen and include chitin-containing fungi that cause apple scab (*Venturia inaequalis*), pepper botrytis (*Botrytis cincerea*), rice blast (*Pyricularia oryzae*), sugar beet cercospora (*Cercospora beticola*), tomato early blight (*Alternaria solani*), wheat leaf rust (*Puccinia recondita tritici*), and wheat powdery mildew (*Erysiphe graminis tritici*). The most potent test compounds in these assays are active in the 10 ppm range.

The following examples are presented to further illustrate and explain the present invention and should not be taken as limiting in any regard.

EXAMPLE 1

This example illustrates a calcofluor rescue screen of this invention. In order to determine the efficacy of the screen of this invention, a large number of compounds are tested, including known chitin synthesis inhibitors in a panel of fungicides selected to represent diverse mechanisms of action.

Components of the test media are first prepared using analytical grade or cell culture tested reagents obtained from the sources indicated in parenthesis.

A mineral salts solution is prepared by mixing

| | |
|---|---|
| MgSO$_4$ (Baker) | 19.6 gm |
| FeCl$_3$.H$_2$O (Baker) | 0.1 gm |
| Distilled Water | 200 ml |

The solution is stored non-sterile.

Yeast basal growth media, YBGM, part A, is prepared by mixing:

| | |
|---|---|
| Glucose (Sigma) | 40 gm |
| Agar (Difco) | 40 gm |
| Distilled Water | 1000 ml | and autoclaving at 20 lbs for 15 minutes. YBGM, part B, is prepared by mixing

| | |
|---|---|
| KH$_2$PO$_4$ (Mallinckrodt) | 27.2 gm |
| KOH (Mallinckrodt) | 6.4 gm |
| (NH$_4$)$_2$SO$_4$ (Sigma) | 4 gm |
| Mineral Salts Solution | 2 ml |
| Distilled Water | 1000 ml | and autoclaving at 20 lbs for 15 minutes. Components A and B are combined after sterilization (denoted as YBGM media) and stored.

A vitamin stock solution is prepared by mixing

| | |
|---|---|
| Pantothenic Acid (Sigma) | 4 mg |
| Pyridoxine.HCl (Sigma) | 4 g |
| Myo-inositol | 20 g |
| Biotin (Sigma, 100 μg/ml stock) | 2.5 ml |
| Thiamine.HCl (Sigma) | 4 mg |
| Distilled Water | 100 ml | and filter sterilizing. The solution is stored at −20° C. in 3 ml aliquots.

A nutrient solution is prepared by mixing

| | |
|---|---|
| Casamino Acids (Difco) | 25 gm |
| Tryptophan (Difco) | 200 gm |
| Uracil (Sigma) | 200 gm |
| Distilled Water | 100 ml | and filter sterilizing. The solution is stored at room temperature protected from the light.

A calcofluor solution is prepared by suspending

| | |
|---|---|
| Calcofluor White (Sigma) | 100 mg |
| in Distilled Water | 5 ml | and adding 25 μl of 10M KOH (Mallinckrodt) to dissolve the calcofluor. An additional 5 ml of distilled water is then added. The solution is stored non-sterile at room temperature.

A yeast extract, peptone, dextrose (YEPD) media for *S. cerevisiae* culture is prepared by mixing

| | |
|---|---|
| Yeast Extract (Difco) | 10 gm |
| Peptone (Difco) | 20 gm |
| Dextrose (Difco) | 20 gm |
| Distilled water | 1000 ml | autoclaving at 20 lbs for 15 min. Strain Y294 having genotype MATα leu2-3,112 ura3-52 his3Δ trp1 GAL+ [CIR+] inoculated into this liquid media and grown overnight, an OD$_{600}$ of ~5 or greater, while being shaken at 30° C.

| | |
|---|---|
| YBGM Media | 1 volume |
| Vitamin Stock Solution | 1/100 volume |
| Nutrient Stock Solution | 1/100 volume |
| Calcofluor White Stock* | 1.25/100 volume |
| Y294 Culture Inoculum | 1/100 volume |

*(10 mg/ml in H$_2$O)

The plates are poured and test samples are placed on the plates. A ¼" disk containing long of nikkomycin Z is used as a positive control. The plates are incubated at 30° C. for two days and then examined for activity. Actives produce a turbid zone surrounding the test sample.

Table I presents a panel of standard fungicides, including both natural and synthetic compounds chosen to represent a wide variety of mechanisms of action.

TABLE I

STANDARD FUNGICIDE PANEL

| Compound | Target |
|---|---|
| amphotericin B | plasma membrane (polyene) |
| cerulenin | fatty acid biosynthesis |
| haloprogin | respiration |
| ketoconazole | ergosterol biosynthesis (lanosterol 14α-demethylase) |
| miconazole | ergosterol biosynthesis (lanosterol 14α-demethylase) |
| dinaconazole | ergosterol biosynthesis (lanosterol 14α-demethylase) |
| econazole | ergosterol biosynthesis (lanosterol 14α-demethylase) |
| fenarimole | ergosterol biosynthesis (sterol Δ14 reductase) |
| tridemorph | ergosterol biosynthesis (sterol Δ14 reductase) |
| tolnaftate | ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin Z | chitin biosynthesis (cell wall) |
| nocodazole | microtubule |
| benomyl | microtubule |
| maneb | multi-target |
| metalaxyl | rRNA biosynthesis |
| vinclozolin | lipid peroxidation |
| kanamycin | mitochondria |
| tunicamycin | glycoprotein biosynthesis |
| carboxin | succinate dehydrogenase |
| cyanobutarate | microtubule (plant) |
| antimycin | respiration |
| 5-fluoro-cytosine | nucleotide metabolism |
| glyphosate | herbicide (aromatic amino acid biosynthesis) |
| phosphinothricin | herbicide (glutamine biosynthesis) |
| aminotriazole | herbicide (histidine biosynthesis) |

TABLE I-continued

STANDARD FUNGICIDE PANEL

| Compound | Target |
|---|---|
| sulfometuron methyl | herbicide (branched chain amino acid biosynthesis) |
| pendimethalin | herbicide (microtubule) |

All compounds are tested by disk diffusion assay using the method of this invention at a rate of 20 μg/disk. None of the compounds are active in the calcofluor rescue screen with the exception of nikkomycin Z. Polyoxin D, a related chitin synthesis inhibitor, is inactive, potentially because the activity of the polyoxins is generally limited to filamentous fungi or because polyoxins are not transported within the cell.

Attempts are made to replace *S. cerevisiae* with several species of filamentous fungi, including *Neurospora crassa, Aspergillus nidulans, Botrytis cinerea, Pseudocercosporella herpotrichoides,* but all the species respond differently from *S. cerevisiae. N. crassa* and *A. nidulans* require very high concentrations of calcofluor to inhibit growth. The cultures exhibit too many false positives, e.g., cyanobutyrate, prowl, 5-F-cytocine, and sulfometuron methyl cause extensive growth besides nikkomycin Z and polyoxin D. *B. cinerea* and *P. herpotrichoides* do not grow in the media and no rescue by nikkomycin Z or polyoxin D is observed.

A control culture of the nikkomycin-producing strain, *Streptomyces cacaoi* var. asoensis is obtained from the the American Type Culture Collection (A.T.C.C. 31160]. This is grown, tested for viability and fermented in a basal medium containing 20 g/l mannitol and 20 g/l soy flour adjusted to a pH of 7.5 with NaOH (designated BM), in BM with added glucose (20 g/L), in BM with added glucose and dried yeast (Nutrex® 2000, 5 g/l) and in BM with glucose and yeast extract (5 g/l). Samples are taken at 30 and 48 hours. No active response is seen in the assay with any fermentation of this culture. No chemical analyses of the fermentations are performed with these samples, so it is not known whether nikkomycin has actually been produced by this culture at levels above the detection limit of the assay.

A panel containing varied antibiotic types (Table II) is tested using the calcofluor rescue screen of this invention using a disk diffusion assay at a rate of 20 μg/disk.

TABLE II

STANDARD ANTIBIOTIC PANEL

| | |
|---|---|
| pimaricin (tennecetin) | streptogramin ("type") |
| monazomycin | nystatin |
| aspartocin | bacitracin |
| clavacin | citrinin |
| avoparcin | isoquinocycline |
| neutramycin | A1531 |
| leucomycin | AO341β |
| angustmycin A & C | gliotoxin |
| gibberellic acid | puromycin |
| puromycin aminonucleoside | BM123α |
| etamycin | mocimycin |
| neomycin | viomycin |
| netropsin | lincomycin |
| picromycin | A9537 |
| AN272α | levomycin |
| AM374 | antiprozoin |
| BL580 zeta | actithiazic acid |
| hamycin | carbomycin |
| frenolicin | fusarinic acid |
| BL580α | tylosin |
| declomycin | tetrahydro spiramycin |
| usnic acid | geldanamycin |
| Z122OA | BM782e |
| BO2964 complex | choramphenicol |
| A8363 | actinomycin |
| BM123γ | AD97 |
| phenazine α | paromomycin |
| streptomycin | A4825 |
| alazopeptin | nucleocidin |
| nonactin | valinomycin |
| C19004 complex | avilamycin |
| V214W | V214X |
| vancomycin | ristocetin |
| relomycin | CO8078α |
| blasticidin S | 4-dedimethylamino-4-methylamino anhydrotetracycline |

None of the compounds listed in Table II have been reported to interfere with fungal cell wall biosynthesis. Consistent with the target specificity of the assay, none of the compounds is active.

The procedure is employed to screen 15,681 compounds and 17,137 fermentation broths. Three actives are identified.

EXAMPLE 2

This example illustrates some secondary in vivo tests and in vitro enzyme assays which are, in some embodiments, employed to retest positives obtained in the primary calcofluor rescue screen of this invention described in Example 1 above.

In Vivo Secondary Screens. The in vivo calcofluor rescue secondary screens assay the differential effect of compounds on the growth of two pairs of yeast strains. Each strain in the pairs, denoted ECY36-3C and ECY36-3D and SSY640-10A and SSY638-3B, is a chitin synthase mutant that relies on the expression of a single chitin synthase isozyme for its survival.

Strains ECY36-3C and ECY36-3D are described by Shaw, J. A., et al., cited above. ECY36-3C has the genotype MATa, chs1-23, chs2::LEU2, ura3-52, leu2-3,112, trp1-1 and ECY36-3D has the genotype MATa, chs1-23, cal$^R$1 (chs3$^-$), ura3-52, leu2-3,112, trp1-1. Both strains are segregants from crossing strain ECY33-18A (Mata, chs1-23, cal$^R$1, ura3-52, leu2-3,112, trp1-1) and ECY19 Δ22 2-5B (MATα, chs1-23, chs2::LEU2, ura3-52, leu2-3,112, trp1-1) using standard methodology. ECY36-3C relies on the expression of chitin synthase isozyme 3 for survival, and ECY36-3D relies on chitin synthase isozyme 2 (Chs2).

Strain SSY640-10A has genotype chs1::HIS3, chs2::TRP1, his3, trp1, ade2, ade3, leu2, lys2, ura3 (possible cmk1Δ 1::HIS3). It is a segregant from a cross between strain 42.1B described by Bulawa, C. E., and Osmond, B. C. *Proc. Natl. Acad. Sci. USA* 87: 7424–7428 (1990), having genotype chs1::HIS3 chs2::TRP1, and a strain with genotype MATα, chs1::HIS3, his3, trp1, ade2, ade3, leu2, lys2, ura3, cmk1Δ 1::HIS3. SSY638-3B has genotype MATα, chs1-23, cal$^R$1(chs3$^-$), ura3, leu2-3,112, trp1-1, ade2-1, his3-11-15 and is derived from a cross between CGY161 having genotype MATα, ade2-1, can1-100, ura3-1, leu2-3, 112, trp1-1, his3-11,15, and ECY36-3D described above. Analogous to the ECY36-3C and ECY36-3D pair, strain SSY638-3B relies on chitin synthase isozyme 2 for survival, whereas SSY640-10 relies on chitin synthase isozyme 3 (Chs3).

Media employed for the secondary screens are as follows:

| | | |
|---|---|---|
| SD | Yeast Nitrogen Base (Difco, without amino acids) | 6.7 g |
| | Dextrose | 20 g |
| | Bacto Agar (Difco) | 20 g |
| | Distilled Water | 1000 ml |
| YEPD | Yeast Extract | 10 g |
| | Peptone | 20 g |
| | Dextrose | 20 g |
| | Distilled Water | 1000 ml |

Strains ECY36-3C and ECY36-3D are inoculated in SD medium containing nutritional supplements appropriate to strain growth, e.g., containing about 0.01% (w/v) each of uracil, adenine sulfate, leucine, tryptophan, histidine, and lysine. When the cultures reach stationary phase (typically after 24 hours), they are used immediately or stored at 4° C. for up to a week before use. The cultures are diluted $\frac{1}{100}$ into YEPD medium containing 2% agar which has been maintained at ~50° C., immediately poured into petri dishes, and allowed to cool. Test compounds are applied to cellulose filter disks as described in Example 1 above (e.g., nikkomycin Z, 4 $\mu$l of a 5 mg/ml solution), and the disks are applied to the agar. Plates are incubated at 30° C. overnight and growth inhibitory zones are measured around the disks after 24 hours.

A number of compounds are tested using this secondary screen, including two compounds that score positive in the calcofluor rescue screen of Example 1 (denoted below as Test Compounds 1 and 2). Filter disks saturated with the compounds dissolved in DMSO (total $\mu$g applied, in parentheses below) are placed on Petri plates containing YEPD agar inoculated with yeast. Zones of inhibition appear after 24 hours. The results are set out in Table III.

TABLE III

| | ECY36-3C | ECY36-3D |
|---|---|---|
| Nikkomycin Z (25 $\mu$g) | 21 mm | 0 |
| Test Compound 1 (45 $\mu$g) | 15.2 mm | 10.8 mm |
| Test Compound 2 (200 $\mu$g) | 15 mm | 0 |

Nikkomycin Z does not inhibit growth of the mutant ECY36-3D that produces only chitin synthase isozyme 2. Nikkomycin Z and several test compounds inhibit the growth of cells that produce only chitin synthase isozyme 3. Some compounds inhibit both kinds of cells, but to different extents. This effect is not due to a non-specific permeability difference between chs2 and chs3 mutants because several known antimicrobial drugs having mechanisims of action unrelated to cell wall biosynthesis display no difference, or have a greater inhibitory effect on chs3 mutants. Similar results are obtained in screens employing SSY640-1-A and SSY638-3B instead of strains ECY36-3C and ECY36-3D.

As a comparison, screens using A.T.C.C. strain S288c (exhibiting genotype MAT$\alpha$, SUC2, mal, mel, gal2, CUP1) exhibit no inhibition with nikkomycin Z or compound 3 (compound 2 is not determined) when tested under the same conditions at the same levels.

In Vitro Secondary Screens. These enzyme assays detect inhibition of individual chitin synthase isozymes Chs1, Chs2, and Chs3 by monitoring the incorporation of radioactive chitin precursor uridine diphospho-N-acetyl glucosamine into acid precipitable counts (i.e., chitin).

In addition to the yeast strains mentioned above, strain JW17-11/1A/FOA is employed. JW17-11/1A has geno-type MATa, chs1::URA3(3), chs2: :LEU2, ura3-52, leu2-3,112. JW17-11/1A/FOA is a 5-fluoroorotic acid induced Ura$^-$ derivative of ascospore JW17-11/1A which itself is derived from diploid JW17-11$\Delta$1, which is homozygous for the same markers but contains one chromosomal disruption of chitin synthase isozyme 2 gene, CHS2 (described by Silverman, S. J., et al., *Proc. Natl. Acad. Sci., U.S.A.*, 85: 4735–4739 (1988)).

To assay Chs3 activity, membranes from cells lacking Chs1 and, preferably, Chs2 are prepared by a modification of the method of Orlean, P. cited above. Strain ECY36-3C, JW17-11/1A/FOA or SSY640-10A are inoculated into YEPD, and the culture is shaken at 30° C. Cells are harvested while still growing exponentially, e.g., at O.D.$_{600}$ of ~0.4 as measured in a Guilford Response™ spectrophotometer, washed once in 50 mM Tris-HCl, pH 7.5, containing 0.01 mM EDTA and 1 mM DTT (1,4-dithiothreitol), and resuspended in about 3 volumes of this buffer. Glass beads of about 200 to 300 micron diameter are added to just below the meniscus of the suspension, and cells are shaken by vortexing or in a Bead-Beater™ until lysis occurs, which is monitored microscopically. During this procedure, the cell suspension is kept below 10° C. by cooling in ice. The extract is collected, the glass beads are washed with the same buffer, and the wash is added to the extract. The volume is adjusted to about 20 original volumes with the same buffer.

The cell walls and debris are removed by a 10 minute centrifugation at about 3000×g. The samples are centrifuged at 100,000×g for 40 minutes at 4° C. The membrane pellets are resuspended in about one original volume 50 mM Tris-HCl, pH 7.5 containing 0.01 mM EDTA which may contain 33% glycerol, and subjected to Dounce homogenization.

Ten $\mu$l of membranes are incubated with shaking in the presence of putative inhibitors in a standard 50 $\mu$l assay mixture containing 1 mM uridine diphospho-($^{14}$C)-N-acetyl-glucosamine (400,000 cpm/$\mu$mole), 40 mM N-acetylglucosamine, 50 mM Tris-HCl, pH 7.5, and 5 mM MgCl$_2$ at 25° C. The reaction is stopped after 90 minutes by addition of 10% trichloroacetic acid, and the amount of product quantified by filtration and scintillation counting.

To assay Chs1 activity, a wild-type strain is employed, as this isozyme is the major in vitro chitin synthase. The procedure for enzyme preparation and enzyme assay is as described below for Chs2 activity.

To measure Chs2 activity, a chs1 mutant is necessary, and a cell that carries a high-copy plasmid with the CHS2 gene such as SSY563-9B simplifies the assay. SSY563-9B is derived from a diploid cell containing both the chs2::LEU2 disruption and multicopy plasmid YEp352-CHS2 as described by Silverman, 1988; the strain has genotype MATa, chs1-23, chs2::LEU2 ura3, leu2-2, trp1-1.

Cells are collected as for the Chs3 assay. For a 250 mg cell pellet (original culture volume of ~100 ml is usually sufficient), 750 $\mu$l of 1% digitonin in 25 mM 2-(N-morpholino) ethane sulfonic acid (MES), pH 6.3, is added, and cells are shaken at 30° C. for 15 minutes. They are centrifuged at 10,000 rpm for 5 minutes, and the pellet is washed with 2.7 ml 25 mM MES, pH 6.3. The pellet is resuspended to a total volume of 750 $\mu$l, and 10 $\mu$l is used per assay.

The cells are first treated with about 1 $\mu$l (experimentally determined to achieve maximum activity) of 1 mg/ml trypsin by shaking at 30° C. for 15 minutes. A two-fold excess of soybean trypsin-inhibitor is added, and the reaction is continued by addition of putative inhibitor test samples, and a standard 50 μl assay mixture of (final concentration) 1 mM uridine diphospho-$^{14}$C-N-acetylglucosamine (400,000 cpm/μmole), 32 mM N-acetylglucosamine, 50 mM Tris-HCl, pH 8 (for Chs 2) or 25 mM MES, pH 6.3 (for Chsl) containing 5 mM cobalt acetate (for Chs2) or 5 mM $MgCl_2$ (for Chs1). Incubations are at 30° C. with shaking. Quantification is as for the Chs3 assay.

Using these procedures, nikkomycin Z is found to act preferentially on the Chs3 isozyme in *S. cerevisiae*. Percentage activity of Chs3 at different levels of nikkomycin Z and polyoxin D are as follows:

| μM inhibitor | % Chs3 Activity |
|---|---|
| 0 μM nikkomycin Z | 100% |
| 1 μM nikkomycin Z | ~80% |
| 2.5 μM nikkomycin Z | ~55% |
| 5 μM nikkomycin Z | ~41% |
| 0 μM polyoxin D | 100% |
| 10 μM polyoxin D | 100% |
| 30 μM polyoxin D | ~40% |
| 90 μM polyoxin D | ~16% |

The secondary screen identifies the affected isozyme, as well as potential artifacts, such as compound—calcofluor complexing. Using secondary screening, compounds testing positive in the primary calcofluor rescue screen appear to affect Chs3 isozymes.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are meant to cover the claimed components and steps in any sequence which is effective to meet the objectives there intended, unless the context specifically indicates the contrary.

BIBLIOGRAPHY

Bulawa, C. E., and Osmond, B. C., *Proc. Natl. Acad. Sci. USA* 87: 7424–7428 (1990).
Cabib, E., *Antimicrob. Agents Chemother.* 35: 170–173 (1991).
Correa, J., et al., *J. Biol. Chem.* 257: 1392–1397 (1982).
Masui, Y., et al., *Biochem. Biophys. Res. Com.* 78: 534–538 (1977).
Neville, A. C., *The Biology of the Arthropod Cuticle*, Springer-Verlag, New York, 1975, pages 71 to 76.
Orlean, P. *J. Biol. Chem.* 262: 5732–5739 (1987).
Roncero, C., and Duran, A., *J. Bact.* 163: 1180–1185 (1985).
Roncero, C., et al., *J. Bact.* 170: 1945–1949 (1988).
Roncero, C., et al., *J. Bact.* 170: 1950–1954 (1988).
Shaw, J. A., et al., *J. Cell Biol.* 114: 111–123 (1991).
Silverman, S. J., et al., *Proc. Natl. Acad. Sci., U.S.A.,* 85: 4735–4739 (1988).

What is claimed is:

1. A method for screening for the presence or absence of chitin synthesis inhibition by a test sample, which comprises:
   (a) adding said test sample to a culture of a fungus that produces chitin, said culture containing calcofluor white or a calcofluor white derivative;
   (b) incubating said test sample in said culture for such time under such conditions sufficient to observe cell growth inhibition in a corresponding culture containing calcofluor white and fungus but no test sample;
   (c) comparing the extent of growth in said culture containing test sample with the extent of growth in said corresponding culture containing no test sample;
   (d) determining the presence of chitin synthesis inhibition by observing whether growth in the presence of test sample exceeds growth in its absence;
   (e) identifying a positive test sample that caused more growth in the presence of said positive test sample than in its absence;
   (f) adding said positive test sample to a second culture of a yeast strain that relies on the expression of a single chitin synthase enzyme for survival;
   (g) incubating the positive test sample in the second culture for such time under such conditions sufficient to observe yeast cell growth in a corresponding second culture containing no test sample;
   (h) comparing the extent of growth in the cultures from steps (f) and (g); and
   (i) determining chitin synthase inhibition by observation of whether growth in the absence of said positive test sample exceeds growth in its presence.

2. A method according to claim 1 further comprising after step (i) a step of determining the level of chitin synthase activity in the presence of said test sample.

3. A method according to claim 1 wherein said fungus that produces chitin is a *Saccharomyces cerevisiae* strain sensitive to calcofluor white.

4. A method according to claim 3 wherein said culture and said corresponding culture exhibit a pH of about 4 to about 8.

5. A method according to claim 4 wherein said calcofluor white is the disodium salt of calcofluor white.

6. A method according to claim 4 further comprising the step of providing, as a control, a *Saccharomyces cerevisiae* culture containing a known chitin synthesis inhibitor but no test sample.

7. A method according to claim 6 wherein said known chitin synthesis inhibitor is nikkomycin.

8. A method according to claim 1 wherein said culture containing test sample and said corresponding culture containing no test sample comprise different portions of a single solidified fungal culture containing calcofluor white.

9. A method according to claim 3 further comprising the step of rescreening test samples in a secondary enzyme assay for chitin synthase activity.

10. A method according to claim 9 wherein said enzyme assay measures uptake of radioactivity labelled uridine diphospho-N-acetylglucosamine into chitin.

11. A method according to claim 9, wherein said secondary enzyme assay comprises an assay selected from the group consisting of an assay for chitin synthase 1, an assay for chitin synthase 2, and an assay for chitin synthase 3.

12. A method according to claim 11 wherein said assay for chitin synthase 2 employs, as a source of the enzyme, a yeast strain that lacks chitin synthase 1 and that carries a high copy plasmid comprising a CHS2 gene.

13. A method according to claim 12 wherein said strain is SSY563-9B.

14. A method according to claim 12 wherein said assay for chitin synthase 3 employs, as a source of the enzyme, a yeast strain that lacks isozymes 1 and 2.

15. A method for screening for the presence or absence of chitin synthesis inhibition by a chemical or biochemical test sample which comprises:

(a) preparing a neutral agar culture media of *Saccharomyces cerevisiae* containing calcofluor white using a strain of *S. cerevisiae* that exhibits growth inhibition when exposed to calcofluor white;

(b) adding to said culture a chemical or biochemical test sample;

(c) incubating said culture containing said chemical or biochemical test sample for such time under such conditions sufficient to observe yeast cell growth inhibition by the calcofluor white;

(d) comparing the extent of growth in the culture at the point of application of said chemical or bioichemical test sample with the extent of growth in the rest of the culture;

(e) determining the presence of said chitin synthesis inhibition by observation of whether growth at the point of application of said chemical or biochemical test sample exceeds growth in the rest of the culture;

(f) identifying a positive test sample that caused more growth at the point of application of said chemical or biochemical test sample than in the rest of the culture;

(g) adding said positive test sample to a second neutral agar culture media of *S. cerevisiae* containing calcofluor white using a strain of *S. cerevisiae* that relies on the expression of a single chitin synthase enzyme for survival;

(h) incubating the positive test sample in the second culture media for such time under such conditions sufficient to observe yeast cell growth at the point of application of said positive test sample;

(i) comparing the extent of growth in the culture at the point of application of said positive test sample with the extent of growth in the rest of the culture; and (j) determining the presence of said chitin synthesis inhibition by observation of whether growth at the point of application of said positive test sample exceeds growth in the rest of the culture.

16. A method according to claim 15 further comprising after step (j) a step of determining the level of chitin synthase activity in the presence of said positive test sample.

17. A method according to claim 15 wherein the agar culture media is solidified, the incubation is carried out in a culture plate, and the determination of whether growth at the point of application of test sample exceeds growth in the rest of the culture is made by observing a turbid zone of growth surrounding the test sample.

18. A method according to claim 17 wherein into said culture is further introduced a known chitin synthesis inhibitor as a positive control.

19. A method according to claim 17 wherein said known chitin synthesis inhibitor is nikkomycin.

20. A method according to claim 17 wherein said *S. cerevisiae* strain is a wild-type 21. A method according to claim 1 further comprising the step of rescreening test samples in a secondary enzyme assay for chitin synthase activity.

22. A method according to claim 21 wherein said enzyme assay measure uptake of radioactivity labeled uridine diphospho-N-acetylglucosamine into chitin.

23. A method for screening for the presence or absence of chitin synthesis inhibition by a chemical or biochemical test sample which comprises:

(a) preparing in a culture plate, a solidified neutral agar culture media of *Saccharomyces cerevisiae* containing the disodium salt of calcofluor white using a strain of *S. cerevisiae* that exhibits growth inhibition when exposed to calcofluor white;

(b) introducing into said culture a chemical or biochemical test sample in a well or on a disk;

(c) introducing into said culture containing said chemical or biochemical test sample a nikkomycin positive control in a well or on a disk;

(d) incubating said culture containing said nikkomycin positive control and said chemical or biochemical test sample for such time under such conditions sufficient to observe yeast cell growth inhibition by the disodium salt of calcofluor white;

(e) comparing the extent of growth in the culture at the point of application of said chemical or biochemical test sample and at the point of application of the positive control with the extent of growth in the rest of the culture;

(f) determining the presence of said chitin synthesis inhibition by observation of whether growth in the vicinity of said chemical or biochemical test sample exceeds growth in the rest of the culture;

(g) identifying a positive test sample that caused more growth at the point of application of said chemical or biochemical test sample than in the rest of the culture;

(h) adding said positive test sample to a second solidified neutral agar culture media of *S. cerevisiae* containing the disodium salt of calcofluor white using a strain of *S. cerevisiae* that relies on the expression of a single chitin synthase enzyme for survival;

(i) incubating the positive test sample in the second culture media for such time under such conditions sufficient to observe yeast cell growth at the point of application of said positive test sample;

(j) comparing the extent of growth in the culture at the point of application of said positive test sample with the extent of growth in the rest of the culture; and (k) determining the presence of said chitin synthesis inhibition by observation of whether growth at the point of application of said positive test sample exceeds growth in the rest of the culture.

24. A method according to claim 23 further comprising after step (k) a step of determining the level of chitin synthase activity in the presence of said positive test sample.

* * * * *